(12) United States Patent
Dillon et al.

(10) Patent No.: US 8,414,293 B2
(45) Date of Patent: Apr. 9, 2013

(54) CARRIER STRIP FOR APPLICATION TO ORAL SURFACES AND RELATED METHODS

(75) Inventors: Rensl Dillon, Ewing, NJ (US); Mahmoud Hassan, Somerset, NJ (US); David B. Viscio, Monmouth Junction, NJ (US); Abdul Gaffar, Princeton, NJ (US); Lisa Christina Beck, League City, TX (US)

(73) Assignee: Colgate-Palmolive Company, New York, NY (US)

( * ) Notice: Subject to any disclaimer, the term of this patent is extended or adjusted under 35 U.S.C. 154(b) by 148 days.

(21) Appl. No.: 11/168,680

(22) Filed: Jun. 28, 2005

(65) Prior Publication Data

US 2006/0292520 A1 Dec. 28, 2006

(51) Int. Cl.
*A61C 19/06* (2006.01)
(52) U.S. Cl. .......................... 433/80; 433/215; 424/401
(58) Field of Classification Search .................. 433/80, 433/215; 424/49, 52, 53, 58, 401
See application file for complete search history.

(56) References Cited

U.S. PATENT DOCUMENTS

| | | | |
|---|---|---|---|
| 1,728,199 A | 9/1929 | Eberhart | |
| 2,310,448 A | 2/1943 | Leib | |
| 2,607,117 A | 8/1952 | Baughan | |
| 2,630,119 A | 3/1953 | Aagesen | |
| 3,754,332 A | 8/1973 | Warren, Jr. | |
| 4,179,815 A | 12/1979 | Hoffman | |
| 5,293,886 A | 3/1994 | Czapor | |
| 5,776,435 A | 7/1998 | Gaffar et al. | |
| 6,290,933 B1 | 9/2001 | Durga et al. | |
| D470,941 S | 2/2003 | Swartz | |
| 6,514,484 B2 | 2/2003 | Rajaiah et al. | |
| 6,551,579 B2 * | 4/2003 | Sagel et al. | 424/53 |
| 6,649,147 B1 | 11/2003 | Ye et al. | |
| 6,649,181 B1 | 11/2003 | Miner | |

(Continued)

FOREIGN PATENT DOCUMENTS

| | | |
|---|---|---|
| JP | 63-154275 U | 10/1988 |
| JP | 2004-538085 A | 12/2004 |

(Continued)

OTHER PUBLICATIONS

Gillen, Robert J. et al. "An Analysis of Selected Normative Tooth Proportions." The International Journal of Prosthodontics. vol. 7, No. 4, 1994.

(Continued)

*Primary Examiner* — Ralph Lewis
(74) *Attorney, Agent, or Firm* — Howard C. Lee

(57) ABSTRACT

An oral carrier strip for the delivery of an oral care composition to the oral cavity of a human or animal subject is provided. The strip includes a first portion adapted to contact a front facing side of a plurality of teeth. A second portion is provided to be folded around the teeth so as to contact a back facing side of the teeth. The first portion has a first perimeter patterned to substantially match a shape of an outer gingival tissue, and the second portion has a second perimeter opposite the first perimeter and patterned to match a shape of an inner gingival tissue. The second perimeter defines an aperture disposed in the second portion having a rounded notch positioned in a center portion of the strip, configured to prevent the strip from tearing when folded around the teeth.

16 Claims, 3 Drawing Sheets

U.S. PATENT DOCUMENTS

| | | |
|---|---|---|
| D485,617 S | 1/2004 | Bosma et al. |
| D485,907 S | 1/2004 | Bosma et al. |
| 6,685,921 B2 | 2/2004 | Lawlor |
| 6,719,995 B2 | 4/2004 | Rajaiah et al. |
| 6,860,736 B2 * | 3/2005 | Allred et al. .............. 433/80 |
| 6,896,518 B2 * | 5/2005 | Jacobs et al. .............. 433/215 |
| D630,328 S | 1/2011 | Fishburne, Jr. |
| D642,267 S | 7/2011 | Dragan |
| D655,007 S | 2/2012 | Dillon et al. |
| 2002/0018754 A1 | 2/2002 | Sagel et al. |
| 2003/0068284 A1 | 4/2003 | Sagel et al. |
| 2003/0206874 A1 | 11/2003 | Doyle et al. |
| 2003/0228264 A1 | 12/2003 | Perna et al. |
| 2004/0002035 A1 | 1/2004 | Jacobs et al. |
| 2004/0005277 A1 | 1/2004 | Willison et al. |
| 2004/0136927 A1 | 7/2004 | Kim et al. |
| 2004/0157192 A1 | 8/2004 | Jacobs et al. |
| 2005/0260544 A1 * | 11/2005 | Jones et al. .............. 433/217.1 |
| 2006/0292520 A1 | 12/2006 | Dillon et al. |
| 2008/0233055 A1 | 9/2008 | Fisher et al. |
| 2009/0060958 A1 | 3/2009 | Mello et al. |
| 2010/0129767 A1 | 5/2010 | Fishburne, Jr. |
| 2010/0304324 A1 | 12/2010 | Dragan et al. |

FOREIGN PATENT DOCUMENTS

| | | |
|---|---|---|
| JP | 2005-017901 A | 1/2005 |
| SU | 938988 | 6/1982 |
| WO | 9516488 A | 6/1995 |
| WO | WO 95/16488 | 6/1995 |
| WO | 03015656 A2 | 2/2003 |
| WO | WO 03/015656 | 2/2003 |
| WO | 2004045569 A | 6/2004 |
| WO | WO 2004/045569 | 6/2004 |
| WO | WO 2004/105629 | 12/2004 |

OTHER PUBLICATIONS

Sterrett, J.D. et al. *"Width/length ratios of normal clinical crowns of the maxillary anterior dentition in man."* Journal of Clinical Periodontology. 1999; 26: 153-157.

Gillen et al., "An Analysis of Selected Normative Tooth Proportions", International Journal of Prosthodontics, Sep.-Oct. 1994; 7(5):410-417.

Sterrett et al., "Width/length ratios of normal clinical crowns of the maxillary anterior dentition in man", Journal of Clinical Periodontology, 1999; 26:153-157.

* cited by examiner

CARRIER STRIP FOR APPLICATION TO ORAL SURFACES AND RELATED METHODS

BACKGROUND OF THE INVENTION

Oral carrier strips are commonly used to provide an oral care composition to the teeth or other surface in the oral cavity. These oral compositions are used for a wide variety of purposes, including the enhancement of hygiene and appearance, and the prevention or treatment of a variety of diseases and other oral cavity conditions in humans and in animals by delivering systemic or localized active agents. The conventional strips typically comprise a plastic film with an oral composition applied to the surface.

The design of such film carriers presents a number of challenges. They must be pharmaceutically and/or cosmetically acceptable for their intended use. Carrier strips must be sized to accommodate a large variation of the dimensions of the teeth and oral cavity of the human and animal subject populations. Conventional carrier strips have several disadvantages: some may be too loose when applied to the dental surfaces, or may bunch up when folded and applied to the front and back portions of the teeth. Carriers having slits to prevent bunching have been known to rip and tear, which adversely affects the delivery function and usefulness of the strip.

In addition to the functional attributes, most consumers expect that the strips will possess and aesthetic appeal. Although such oral carrier strips have generally met with consumer approval, the art seeks to further improve the aesthetic effects as well as the cosmetic and therapeutic benefits. Thus remains a need in the art for improved oral carrier strips, and methods of their use.

BRIEF SUMMARY OF THE INVENTION

The invention provides an oral carrier strip including (i) a first portion having a proximal longitudinal perimeter and (ii) a second portion having a distal longitudinal perimeter. The distal longitudinal perimeter defines a rounded notch.

Also included are oral carrier strips including a first portion adapted to contact a front facing side of a plurality of teeth and having a first perimeter patterned to substantially match a shape of an outer gingival tissue; and a second portion adapted to be folded around the teeth so as to contact a back facing side of the teeth, the second portion having a second perimeter opposite the first perimeter and patterned to match a shape of an inner gingival tissue. The second portion has a rounded notch positioned in a center portion of the strip.

In another embodiment, the invention provides an oral carrier strip including a first portion having a proximal longitudinal perimeter, and a second portion having a distal longitudinal perimeter. The distal longitudinal perimeter contains a notch that is adapted to inhibit tearing of the strip upon application.

Related kits and methods are also provided.

BRIEF DESCRIPTION OF THE DRAWINGS

The present invention will become more fully understood from the description and the accompanying drawings.

DETAILED DESCRIPTION OF THE INVENTION

Figure 1A:
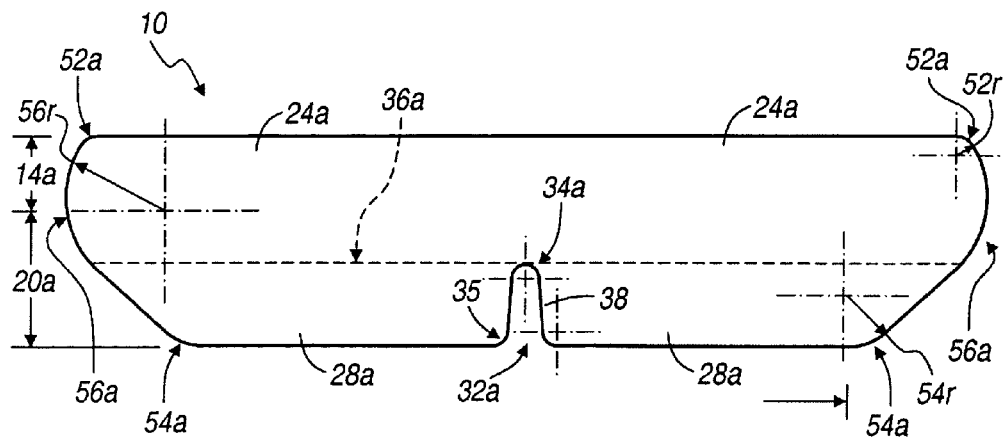
FIG. 1A is a plan view illustrating an oral carrier strip configured for the upper teeth of a subject according to the principles of the present invention.

The present invention provides shaped oral carrier strips that are useful for delivery of active agents to the oral surfaces, such as the teeth and gums, and to the oral cavity. The invention also relates to methods of administration of active agents or oral care compositions to the dental surfaces using the oral carrier strips of the invention. It has been discovered that the oral carrier strips of this invention afford advantages over the carrier strips among those known in the art. Such advantages include providing a carrier strip that is resistant to tearing when folded from the front to the back portion of the teeth surfaces. Further uses, benefits, and embodiments of the present invention are apparent from the description set forth herein.

The term "oral cavity" as used herein refers to the cavity bounded by the lips and the epiglottis in vertebrates. The oral cavity includes "hard tissues," such as the teeth and periodontal support, and "soft tissues," such as the gums and gingiva, the tongue, and the surfaces of the buccal cavity. Within the scope of this application, an "oral surface" includes the hard and soft tissues of the oral cavity.

The carrier strips of the invention may be fabricated of rigid or flexible materials, comprising any of a variety of orally or cosmetically acceptable materials, i.e., materials that are suitable for use with humans and/or animals to provide the desired benefit without undue adverse effects (such as toxicity, irritation, and allergic response) commensurate with a reasonable benefit/risk ratio. Exemplary materials may include polymer/copolymer films (thermoset polymers, thermoplastic polymers), papers, waxes, textiles (non-woven and woven), clays, foils, gels and wood composites and combinations of the same. For example, a strip can comprise a first layer comprising a polymer and/or an adhesive, a second layer that comprises an oral care active or functional composition, and one or more additional layers that provide additional ingredients or a coating. The coating can be, for example, a shellac coating. A coating can comprise a layer on either or both sides of a polymer or intermediate layer.

Specific polymers suitable for use as the strip material include cellulose ethers, methacrylates, polyvinylpyrrolidone, hydroxyalkyl cellulose polymers, such as hydroxypropyl methyl cellulose (HPMC), hydroxypropyl cellulose, hydroxyethyl cellulose, methyl cellulose, carboxymethyl cellulose; polyvinylpyrrolidone, cross-linked polyvinyl pyrrolidone, polyvinylpyrrolidone-vinyl acetate copolymer, polyvinyl alcohol, polyacrylic acid, poly acrylate polymer, cross-linked polyacrylate polymer, cross-linked polyacrylic acid (e.g., CARBOPOL® available from Noveon, Inc., Cleveland, Ohio, United States of America), polyethylene oxide, polyethylene glycol, poly vinylalkyl ether-maleic acid copolymer (such as GANTREZ® available from ISP Corporation, Wayne N.J., United States of America) and carboxy vinyl polymers; marine colloids and natural gums, such as sodium alginate, carrageenan, xanthan gum, gum acacia, arabic gum, guar gum, pullulan, agar, chitin, chitosan, pectin, karaya gum, zein, hordein, gliadin, locust bean gum, tragacanth and other polysaccharides; starches such as maltodextrin, amylose, high amylose starch, corn starch, potato starch, rice starch, tapioca starch, pea starch, sweet potato starch, barley starch, wheat starch, waxy corn starch, modified starch (e.g., hydroxypropylated high amylose starch), dextrin, levan, elsinan and gluten; and proteins such as collagen, whey protein isolate, casein, milk protein, soy protein, gelatin, and waxes and rosins, such as synthetic waxes and beeswax.

Other suitable polymers may include modified starches, cellulose acetate, cellulose nitrate, ethylene-vinyl acetate copolymers, vinyl acetate homopolymer, ethyl cellulose, butyl cellulose, isopropyl cellulose, shellac, silicone polymer (e.g., dimethylsilicone), PMMA (poly methyl methacrylate), cellulose acetate phthalate and natural or synthetic rubber; polymers insoluble in organic solvents, such as cellulose, polyethylene, polypropylene, polyesters, polyurethane and nylon.

The carrier strips of the invention may contain various inorganic materials, such as mica, mica coated with titanium dioxide, clay, and mother-of-pearl. In some embodiments, the film forming material comprises graphite. In various embodiments, a film forming material may include a hydrophobic organic non-polymeric material such as a wax, for example, beeswax or paraffin.

The carrier strips of the invention can be formulated of materials such that they disintegrate within a time period after placement on an oral surface. The strips may release an active agent into the oral cavity prior to disintegrating and/or the release of the active agents may occur subsequent to the disintegration. The disintegration of the carrier strip may be through any means, such as mechanical, chemical (dissolution or as a result of a chemical reaction occurring upon placement on an oral surface), or physical-chemical means. The disintegration can result, for example, from shearing, grinding, or exposure to elevated temperatures during use.

Carrier strips of the invention may disintegrate into small pieces that are not visually discernable or disintegrate to collectively form a colloid or gel. Alternatively, the polymer of the carrier is a breakable water soluble polymer that dissolves during use. The dissolution can occur as a result of, for example, mechanical means, and/or exposure to a solvent comprising a high concentration of water, such as saliva. In some embodiments, the polymer is insoluble but breakable in water by being dispersible, i.e., the polymer breaks down into small fragments, or the polymer is insoluble but is water swellable. In configurations in which a polymer does not break down during use, the polymer can be a water-repellant polymer or an aqueous-stable hydrophilic polymer such as certain types of cellulose, for example paper. In some embodiments, the strip can comprise a mixture of film forming materials.

The carrier strips of the present invention optionally comprise materials that affect the physical or functional characteristics of the strip. Such additional substances can be, for example, surfactants, emulsifiers, plasticizers, fillers, or thickeners or other texture modifiers. Fillers among those useful herein include inert starch particles and cellulose. Texture modifiers include water swellable, physically modified and pregelatinized starches, to increase the stiffness of polymeric films, such as those comprising hydroxyalkyl methyl cellulose. In the preparation of such starch products, the granular starch is preferably cooked in the presence of water and, optionally, an organic solvent at a temperature not higher than 10° C. higher than the gelatinization temperature. The obtained starch is then dried. Pregelatinized corn starch useful herein is available commercially.

Embodiments of this invention comprise one or more oral carrier strips. As referred to herein, a "strip" is a material having a substantially lamellar structure. A "lamellar" structure has, or is capable of having, a size in one or two dimensions (e.g., the x- or y-dimensions) that is substantially greater than the thickness of the structure in a third dimension (e.g., the z-direction). Lamellar structures among those useful herein include those that are substantially planar, layered, or lamelliform. In one embodiment, the lamellar structure is substantially planar, having a size in both the x- and y-dimensions that is substantially greater than the z-direction. In other embodiments, the lamellar structure is non-planar. In certain embodiments, the strips of this invention comprise a substantially continuous surface that can appear as a substantially flat surface, although in some embodiments the strip is slightly deformed or curved. In such embodiments, the strip can have any of a number of shapes, including having a smooth curved surface.

The strips have a lamellar structure (further described below), but such structure may be composed of a single layer of material or multiple layers of material. If more than one layer of materials is present in the strip, the layers may be affixed to one another by any means, including lamination, application of an intervening adhesive layer(s), or application of the additional layer by coating, such that the layers are bonded to one another.

Figure 1B:
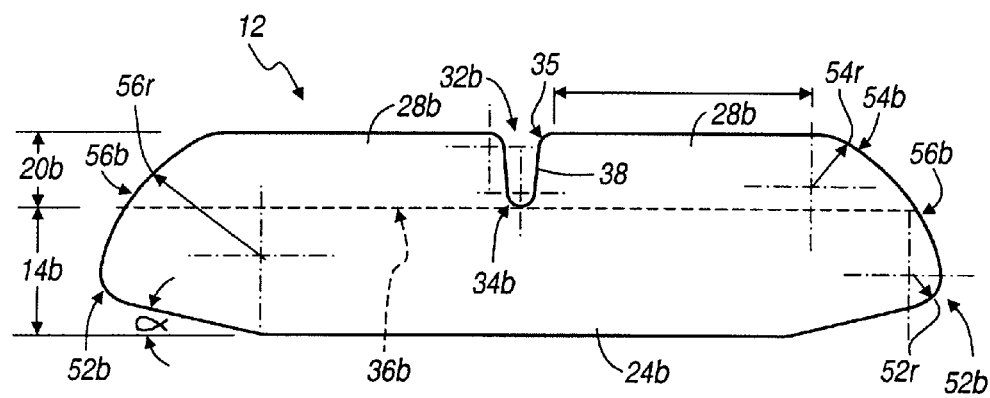
FIG. 1B is a plan view illustrating an oral carrier strip configured for the lower teeth of a subject according to the principles of the present invention.

FIGS. 1A and 1B are plan views illustrating an oral carrier strip configured for the upper and lower teeth of a subject, respectively designated with reference numerals 10 and 12, according to the principles of the present invention. For simplicity, certain features that are common to, or shared by, the carrier strips 10, 12 or their environment in the oral cavity, are generally referred to by the same reference numbers. It should be understood that in certain descriptions, while the discussion may be specifically directed to the upper 10 or lower 12 carrier strip, the overall design may be applicable to both carrier strips 10, 12. Additionally, while specific reference may be made explicitly to certain figures throughout the specification, attention should be made to all of the figures, as certain figures may depict or illustrate certain features or aspects of the present invention while not specifically being referred to.

Figure 2A:
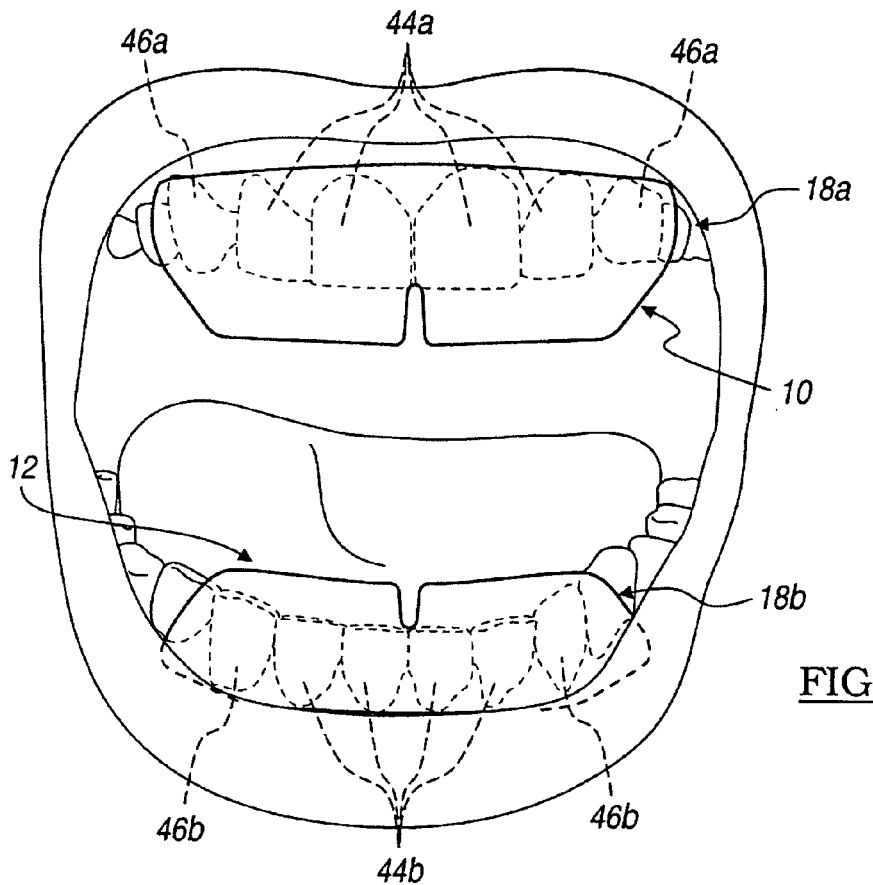
FIG. 2A is a perspective view illustrating the oral carrier strips being applied to the upper and lower teeth of a human subject.
Figure 3:
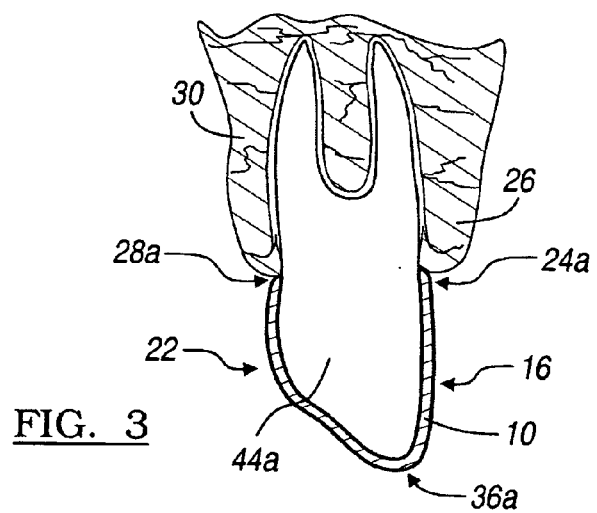
FIG. 3 is a magnified cross-sectional view of FIG. 2C taken through line 3-3 illustrating the oral carrier strip folded over a tooth and adjacent the gingival surfaces.

With reference to FIGS. 1-3, the upper oral carrier strip 10 has a first portion 14a adapted to contact a front facing side 16 of a plurality of upper teeth 18a, and a second portion 20a adapted to be folded so as to contact a back facing side 22 of the plurality of teeth 18a. The upper strip 10 has a first, or proximal, perimeter 24a patterned to substantially match a shape of an outer gingival tissue 26, and a second, or distal, perimeter 28a patterned to substantially match a shape of an inner gingival tissue 30. The second perimeter 28a is shaped to define an aperture 32a disposed in the second portion 20a of the strip 10 having a rounded notch 34a positioned in a center location or portion of the strip 10. In certain embodiments, the rounded notch 34a is located at a medial location between the first 24a and second 28a perimeters.

Similarly, the lower oral carrier strip 12, has a first portion 14b adapted to contact a front facing side 16 of a plurality of lower teeth 18b, and a second portion 20b adapted to be folded so as to contact a back facing side 22 of the plurality of teeth 18b. The lower strip 12 has a first, or proximal perimeter 24b patterned to substantially match a shape of an outer gingival tissue 26, and a second or distal perimeter 28b patterned to substantially match a shape of an inner gingival tissue 30. The second perimeter 28b is shaped to define an aperture 32b disposed in the second portion 20b of the strip 12 having a rounded notch 34b positioned in a center portion of the strip 12. In certain embodiments, the rounded notch 34b is located at a midpoint area, or medial location between the first 24b and second 28b perimeters.

Figure 1C:
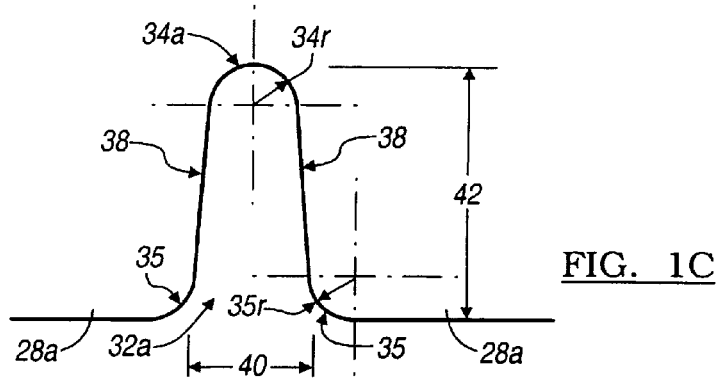
FIG. 1C is a magnified view illustrating an aperture and rounded notch of FIG. 1A.

FIG. 1C is a magnified view illustrating the aperture 32a of FIG. 1A. As shown, the aperture 32a is defined by the second perimeter 28a and includes two rounded corners 35 adjacent substantially linear wall regions 38 that preferably taper slightly inward towards a rounded notch 34a. In various embodiments, the notch is configured so as to prevent the strip from tearing when folded around the teeth; i.e., to substantially minimize or eliminate the incidence of tearing during typical conditions of use. In preferred embodiments, the notch 34a is configured to be substantially rounded, for example, semi-circular or oval shaped, thereby minimizing or preventing the strip 10 from tearing when folded around the teeth 18a. While other shapes may be suitable, it is preferred that the notch does not have straight angle cuts. One function of the aperture 32a is to allow the second portion 20a to be folded around to the back side 22 of the teeth 18a with minimal bunching or folding of material. Another advantage is that the aperture 32a can be used by the user to align the strip with the center of the teeth without other graphical indicia such as lines or arrows, thus allowing proper alignment within the oral cavity. In various embodiments, the aperture 32a has a width 40 from about 1.5 to about 3 mm in length, and a height 42 from about 3 to about 8 mm in length. The rounded notch 34a preferably has a radius of curvature 34r from about 0.5 to about 2 mm, preferably from about 0.75 to about 1.5 mm. The corners 35 preferably have a radius of curvature 35r from about 0.5 to about 2.5 mm and will depend upon the specific design. In one preferred embodiment, the height 42 of the aperture 32a is about 6 mm, and the radius of curvature 34r of the rounded notch 34a is about 0.8 mm. The specific dimensions will vary slightly depending upon desired application, along with the mean tooth sizes of the populations the strips are designed for use with. Moreover, it should be understood that while FIG. 1C specifically depicts the aperture 32a and rounded notch 34a of the upper carrier strip 10, the dimensions and discussion are equally applicable to the aperture 32b and rounded notch 34b of the lower carrier strip 12.

Referring to FIGS. 1A and 1B, in various embodiments, the oral carrier strips 10, 12 have a substantially horizontal, or longitudinal, fold 36a, 36b separating the respective first 14a, 14b and second 20a, 20b portions. In certain embodiments, the fold 36a, 36b may be perforated to assist a user in folding the second portion 20a, 20b around to the back facing side 22 of the teeth 18a, 18b. In other embodiments, the fold may be a graphical indicia of a different color, for example, a red or black line, arrow, or the like. In certain preferred embodiments, the rounded notch 34a, 34b is co-joined with, the fold 36a, 36b.

FIG. 2A is a perspective view illustrating the oral carrier strips 10, 12 being applied to the upper 18a and lower teeth 18b, respectively, of a human subject. In various preferred embodiments of the present invention, the carrier strips 10, 12 extend a length operable to contact at least 6 to 8 teeth, preferably including the upper and lower incisors 44a, 44b and canine 46a, 46b teeth, respectively. In certain embodiments, the upper strips 10 can range in length from about 60 mm up to about 75 mm in the longest dimension. Similarly, the lower strips 12 can range in length from about 40 mm up to about 65 mm in the longest dimension. As referred to herein, a "long dimension" is the dimension of the strip in length or width (i.e., in the x- and y-dimensions, as the strip is, or is deformed to be, in a planar shape) in a dimension substantially perpendicular to the "thickness" or shortest dimension of the strip (i.e., the z-dimension). It should be understood that in certain instances, it may be desirable to have shorter or longer strips 10, 12 depending upon use and the subject population.

Figure 2B:
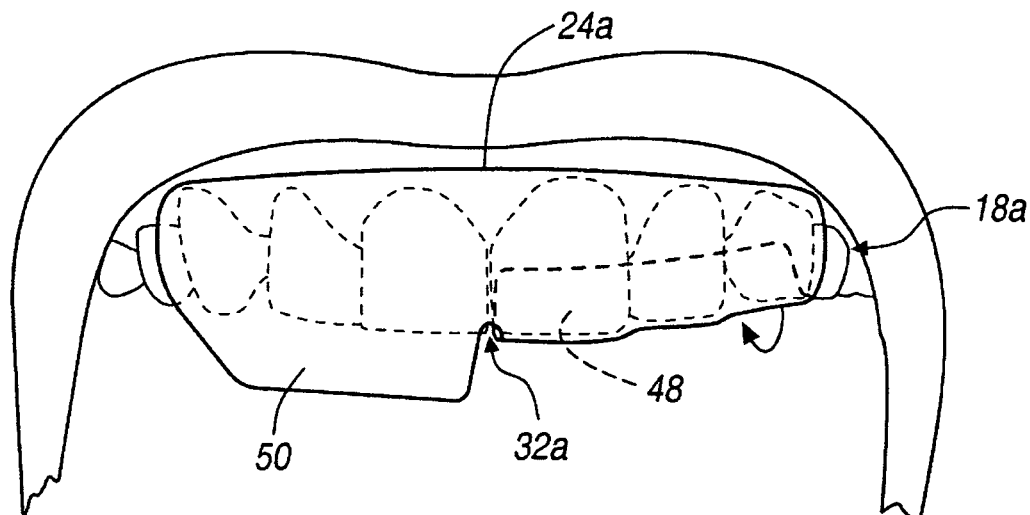
FIG. 2B is a partial perspective view of FIG. 2A illustrating the oral carrier strip in the process of being folded over the upper teeth and adjusted for treatment.
Figure 2C:
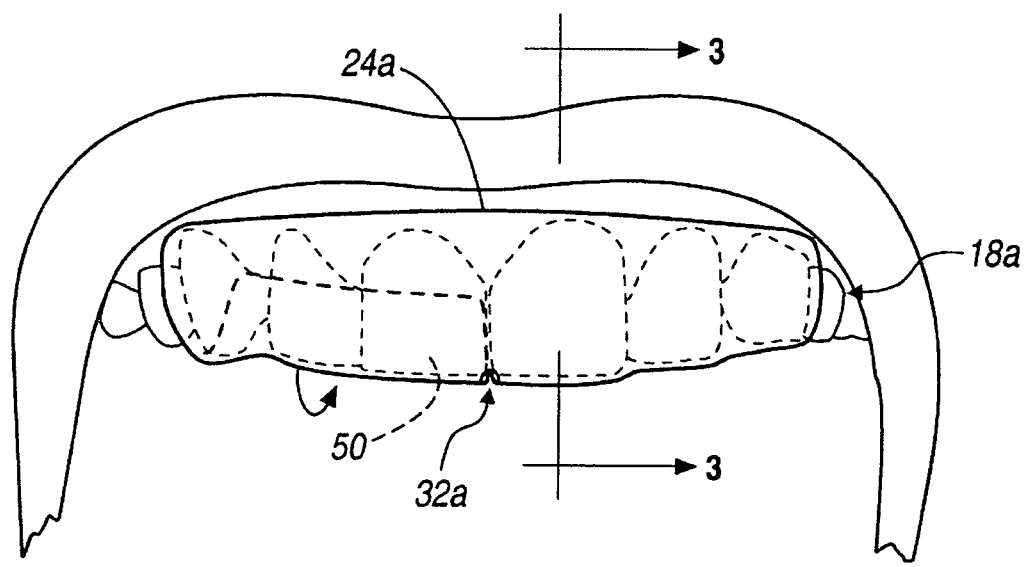
FIG. 2C is a partial perspective view of FIG. 2A illustrating the oral carrier strip being fully folded over the upper teeth and adjusted for treatment.

FIG. 2B is a partial perspective view of FIG. 2A illustrating the oral carrier strip 10 in the process of being folded over the upper teeth 18a. Preferably the aperture 32a is aligned between the central incisor teeth 44a. The first portion 14a is pressed upon the front facing side 16 of the teeth 118a and light pressure is applied. After the strip 10 is properly aligned and placed on the front facing side 16, a first half 48 of the second portion 20a is folded over and pressed onto the back facing side 22 of the teeth 18a and adjusted as necessary for form and comfort during treatment. Subsequently, as shown in FIG. 2C, a second half 50 of the oral carrier strip 10 is folded over the remaining upper teeth 18a and adjusted for treatment. It should be noted that the order in which the portions 48, 50 of the strip 10 are folded over does not matter, and both halves 48, 50 may be folded over at the same time, if so desired.

In various embodiments, the first 24a, 24b and second 28a, 28b perimeters are substantially linear. In other embodiments, at least one of the perimeters 24a, 24b, 28a, 28b is non-linear, for example, angled or substantially arcuate in shape, and better configured to be applied to the upper 18a or lower 18b teeth and matched to the gingival areas 26, 30. In certain embodiments, the carrier strips 10, 12 have a first portion 14a, 14b with first and second opposite rounded corners 52a, 52b having a radius of curvature 52r from about 1.5 to about 2.5 mm. Likewise, in certain embodiments, the carrier strips 10, 12 have a second portion 20a, 20b with first and second opposite rounded corners 54a, 54b having a radius of curvature 54r from about 4 to about 5 mm. In one embodiment, the first perimeter 24b of the lower strip 12 is provided with three areas slightly angled from one another wherein angle α is from about 5 to about 15 degrees. Preferably the carrier strip 10, 12 side regions 56a, 56b are also substantially rounded in shape, having a radius of curvature 56r from about 5 to about 15 mm, preferably from about 8 to about 12 mm.

FIG. 3 is a magnified cross-sectional view of FIG. 2C illustrating the upper carrier strip 10 folded over a tooth 44a. In various preferred embodiments, the strips are sized having a width that will accommodate twice the mean height of the canine and incisor tooth lengths for a given subject population. In certain embodiments, for example, the width is from about 10 to about 20 mm in length, preferably, the width is about 15 mm. As shown, the first perimeter 24a is patterned to be adjacent to, or conjoins the outer gingiva 26 tissue, and the second perimeter 28a is patterned to be adjacent to, or conjoins the inner gingiva tissue 30. In certain embodiments, the first 24a and second 28a perimeters overlap a portion of the respective outer 26 and inner 30 gingiva tissues (not shown).

In various embodiments, the carrier strips 10, 12 of the present invention have a thickness of from about 20 microns to about 750 microns. In certain preferred embodiments, the strips 10, 12 have a thickness of from about 20 microns up to about 250 microns, or from about 100 microns up to about 200 microns, preferably from about 150 microns up to about 175 microns.

Kits according to various embodiments of the present invention comprise both an upper 10 and a lower 12 carrier strip as described herein, each having an oral composition thereon. The oral compositions may be the same on both strips, or they may be different. The kits may contain a single strip 10, 12 for the upper 18a and lower 18b teeth, or they may also include various combinations of the strips 10, 12 in the same or different quantities. Instructions for using the kit and optimizing the use of the carriers may also be provided.

The carrier strip as described above may "carrie" an oral care composition for delivery of such agent/compositions to the dental surface(s) upon contact or it may be impregnated with such compositions(s). "Contact" of the strip to the dental surfaces is meant to include those situations where the strip is coated with the composition and the composition contacts the dental surface. An "oral care active agent" is a material having a desired utility for oral care. The agent may have one or more of a therapeutic, cosmetic, aesthetic, decorative, sensory, prophylactic, or diagnostic utility. Active agents can include sulfur precipitating agents, pharmaceuticals cosmetic actives, natural extracts and essential oils, sensory agents, stain prevention actives, conditioning agents, moisturizers, and combinations thereof. Such active agents may be included or impregnated in the strip, or may be a coating or layer on the strip.

Cosmetic and pharmaceuticals active agents include those which act either systemically and/or locally to provide a therapeutic, diagnostic and/or prophylactic effect or act to enhance the appearance of the oral surface or to reduce or eliminate breath or mouth odor. Active agents are disclosed in, e.g., U.S. Patent Publication 2003/0206874, Doyle et al., published Nov. 6, 2003; U.S. Pat. No. 6,290,933, Durga et al., issued Sep. 18, 2001; and U.S. Pat. No. 6,685,921, Lawlor, issued Feb. 3, 2004, the contents of each of which are incorporated herein by reference.

In various embodiments, the oral compositions of the present invention comprise a whitening agent. A "whitening agent" is a material which is effective to effect whitening of a tooth surface to which it is applied. In various embodiments, the compositions of this invention comprise a peroxide whitening agent, comprising a peroxide compound. As referred to herein, a "peroxide compound" is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide, glyceryl hydrogen peroxide, alkyl hydrogen peroxides, dialkyl peroxides, alkyl peroxy acids, peroxy esters, diacyl peroxides, benzoyl peroxide, hydrogen peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof.

An antibacterial agent may be included. Any orally acceptable antimicrobial agent can be used, including triclosan (5-chloro-2-(2,4-dichlorophenoxy)phenol); 8-hydroxyquinoline and salts thereof; zinc and stannous ion sources such as zinc citrate, zinc sulphate, zinc glycinate, sodium zinc citrate and stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride); bisguanides, such as chlorhexidine digluconate, hexetidine, octenidine, alexidine; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; magnolia extract; grapeseed extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and clindamycin; and mixtures thereof. A further illustrative list of useful antibacterial agents is provided in U.S. Pat. No. 5,776,435, Gaffar, et al., issued Jul. 7, 1998, the contents of which are incorporated herein by reference.

The strips of the present invention may be made in a variety of ways, including methods among those known in the art for making strips or films. In certain embodiments, the carrier strip comprises a backing layer and an oral composition. For example, the components of a film forming oral composition slurry are mixed to form a slurry composition, cast or applied to the backing layer, and subsequently dried. Drying of the slurry can be carried out at high temperature with the aid of a drying oven, a drying terminal, a vacuum drier, or any other suitable drying equipment known in the art. Once dry, the carrier strips are stamped or cut to size using dies or the like.

In another embodiment, the slurry is cast on a releasable substrate and dried to form a sheet of film material. Preferably, the substrate material has a surface tension that allows the film slurry to spread substantially uniformly across the substrate surface, thereby avoiding formation of a destructive bond between the film and the substrate. Non-limiting examples of suitable substrates include glass, stainless steel, Polytetrafluoroethylene, and polyethylene- or silicone-impregnated paper. Following casting, the film is then dried as previously detailed. In other embodiments, the film is made by extrusion of the film composition through a die, followed by cutting to a desired pattern, and drying. In other embodiments, the film is made by solvent casting.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

We claim:

1. An oral carrier strip comprising:
   a first portion having a proximal longitudinal perimeter, and
   a second portion having a distal longitudinal perimeter,
   wherein the distal longitudinal perimeter comprises no more than one notch, the notch being rounded and located at a center location of the distal longitudinal perimeter, and wherein the rounded notch (a) has a radius of curvature at a rounded end from about 0.5 to about 1.5 mm, (b) has a substantially constant width that is about 1.5 to about 3 mm, and (c) is about 3 to about 8 mm in length and wherein the rounded notch extends inwardly from the distal longitudinal perimeter to adjacent a line along which the oral carrier strip is folded.

2. An oral carrier strip according to claim 1, further comprising a fold separating the first and second portions.

3. An oral carrier strip according to claim 2, wherein the fold is perforated.

4. An oral carrier strip according to claim 1, having a thickness from about 20 to about 250 microns.

5. An oral carrier strip according to claim 1, wherein the strip comprises an oral composition selected from the group consisting of whitening agents, antibacterial agents, antimicrobial agents, anti-gingivitis agents, anti-caries agents, anti-tartar agents, antiplaque agents, desensitizing agents, malodor control agents, salivary stimulants, periodontal actives, natural extracts and essential oils, enzymes, anti-inflammatory agents, anti-viral agents, nutrients, antioxidants, analgesics, and combinations thereof.

6. An oral carrier strip according to claim 1, further comprising a substantially horizontal fold separating the first and second portions.

7. An oral carrier strip according to claim 1, extending a length operable to contact at least 6 to 8 teeth of a human.

8. An oral carrier strip according to claim 1, extending a length operable to contact the canine and incisor teeth of a human.

9. An oral carrier strip according to claim 1, wherein the first portion has a long dimension from about 60 to about 75 mm.

10. An oral carrier strip according to claim 1, wherein the first perimeter has a substantially arcuate shape.

11. An oral carrier strip according to claim 1, having a width such that at least one of the first and second perimeters overlap a portion of gingival tissue when the strip is positioned on the oral hard surface.

12. An oral carrier strip according to claim 1, having a width such that the first and second perimeters conjoin the edges the gingival tissue, when the strip is positioned on the oral hard surface.

13. An oral carrier strip according to claim 1, wherein the first portion comprises first and second opposite rounded corners having a radius of curvature from about 1.5 to about 2.5 mm.

14. An oral carrier strip according to claim 1, wherein the second portion comprises first and second opposite rounded corners having a radius of curvature from about 4 to about 5 mm.

15. An oral carrier strip according to claim 1, comprising more than one layer of material.

16. An oral carrier strip according to claim 1, wherein the strip disintegrates during use.

\* \* \* \* \*